United States Patent
Spreigl et al.

[11] Patent Number: 6,161,029
[45] Date of Patent: Dec. 12, 2000

[54] APPARATUS AND METHOD FOR FIXING ELECTRODES IN A BLOOD VESSEL

[75] Inventors: William T. Spreigl, Andover; Douglas N Hess, Maple Grove, both of Minn.; Henri G. Heynen, Geleen, Netherlands; Chester I. Struble, Ph Eijsden, Netherlands; Paulus C. von Venrooij, Hoenabroek, Netherlands

[73] Assignee: Medtronic, Inc., Minneapolis, Minn.

[21] Appl. No.: 09/265,445

[22] Filed: Mar. 8, 1999

[51] Int. Cl.[7] ............................. A61B 5/042; A61N 1/05
[52] U.S. Cl. ........................... 600/381; 600/375; 607/126
[58] Field of Search ................................. 600/374, 381, 600/375; 607/122, 126

[56] References Cited

U.S. PATENT DOCUMENTS

| | | |
|---|---|---|
| 3,788,329 | 1/1974 | Friedman . |
| 4,414,986 | 11/1983 | Dickhudt et al. . |
| 4,553,545 | 11/1985 | Maass et al. . |
| 4,706,671 | 11/1987 | Weinrib . |
| 4,733,665 | 3/1988 | Palmaz . |
| 4,825,871 | 5/1989 | Cansell . |
| 4,852,573 | 8/1989 | Kennedy . |
| 4,860,769 | 8/1989 | Fogarty et al. . |
| 4,886,062 | 12/1989 | Wiktor . |
| 4,969,458 | 11/1990 | Wiktor . |
| 5,007,435 | 4/1991 | Doan et al. . |
| 5,016,808 | 5/1991 | Heil, Jr. et al. . |
| 5,037,427 | 8/1991 | Harada et al. . |
| 5,170,802 | 12/1992 | Mehra . |
| 5,174,288 | 12/1992 | Bardy et al. . |
| 5,221,261 | 6/1993 | Termin et al. . |
| 5,224,491 | 7/1993 | Mehra . |
| 5,235,977 | 8/1993 | Hirschberg et al. . |
| 5,242,451 | 9/1993 | Harada et al. . |
| 5,246,014 | 9/1993 | Williams et al. . |
| 5,255,691 | 10/1993 | Otten . |
| 5,256,146 | 10/1993 | Ensminger et al. . |
| 5,279,299 | 1/1994 | Imran . |
| 5,306,294 | 4/1994 | Winston et al. . |
| 5,372,600 | 12/1994 | Beyar et al. . |
| 5,387,233 | 2/1995 | Alferness et al. . |
| 5,411,546 | 5/1995 | Bowald et al. . |
| 5,423,865 | 6/1995 | Bowald et al. . |
| 5,476,498 | 12/1995 | Ayers . |
| 5,531,779 | 7/1996 | Dahl et al. . |
| 5,954,761 | 9/1999 | Machek et al. ........................ 607/126 |
| B1 4,733,665 | 1/1994 | Palmaz . |

*Primary Examiner*—Lee Cohen
*Attorney, Agent, or Firm*—Reed A. Duthler; Harold R. Patton

[57] ABSTRACT

Endocardial implantable cardiac leads are disclosed for applying electrical stimulation to and/or sensing electrical activity of the heart at one or more distal electrode positioned at a cardiac implantation site within a cardiac vessel adjacent to and at a desired orientation to the left ventricle or atrium of the heart. The distal electrode(s) is supported by a tubular electrode support having a diameter large enough to bear against the blood vessel wall and a support lumen that allows blood to flow through it. A retention stent extends proximally from a distal stent end fixed to the tubular electrode support to a proximal stent end. After advancement to the cardiac implantation site employing a lead delivery mechanism, the retention stent is expandable from a collapsed stent state in which the outer diameter of the retention stent is less than the inner diameter of the vessel to an expanded stent state. The expanded stent is lodged against the blood vessel wall and inhibits movement of the stent and distal electrode support. The expanded stent lumen is aligned with the electrode support lumen for allowing blood to flow through the aligned electrode support lumen and expanded stent lumen. The retention stent may take any of the known forms that can be introduced in the collapsed stent state within an introducer lumen or mounted to an introducer and can either self-expand upon release in the blood vessel or be mechanically expanded within the blood vessel.

25 Claims, 9 Drawing Sheets

FIG. I

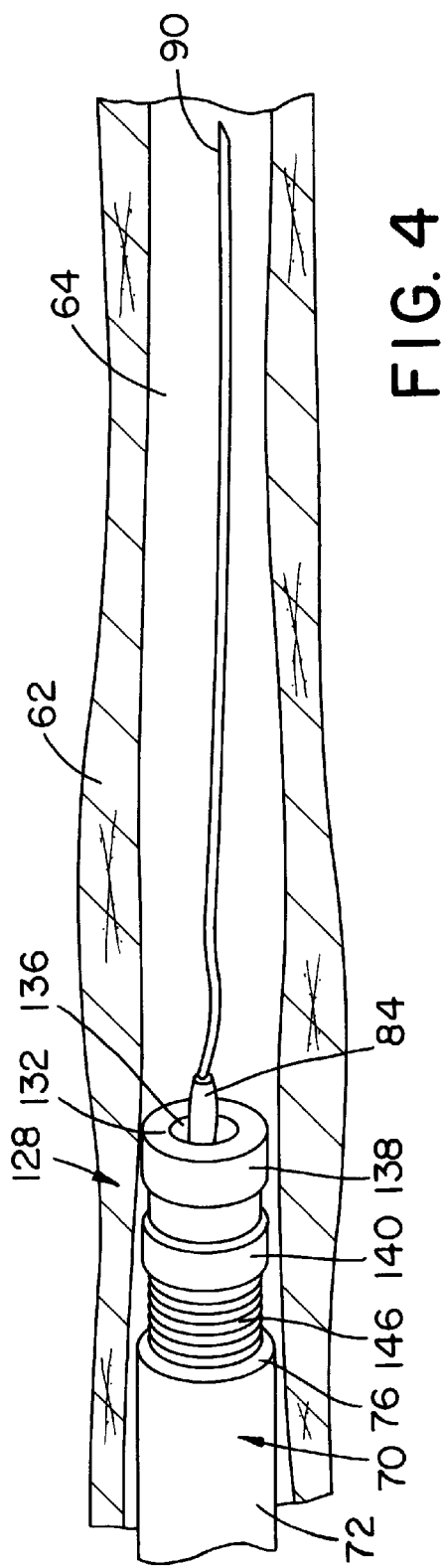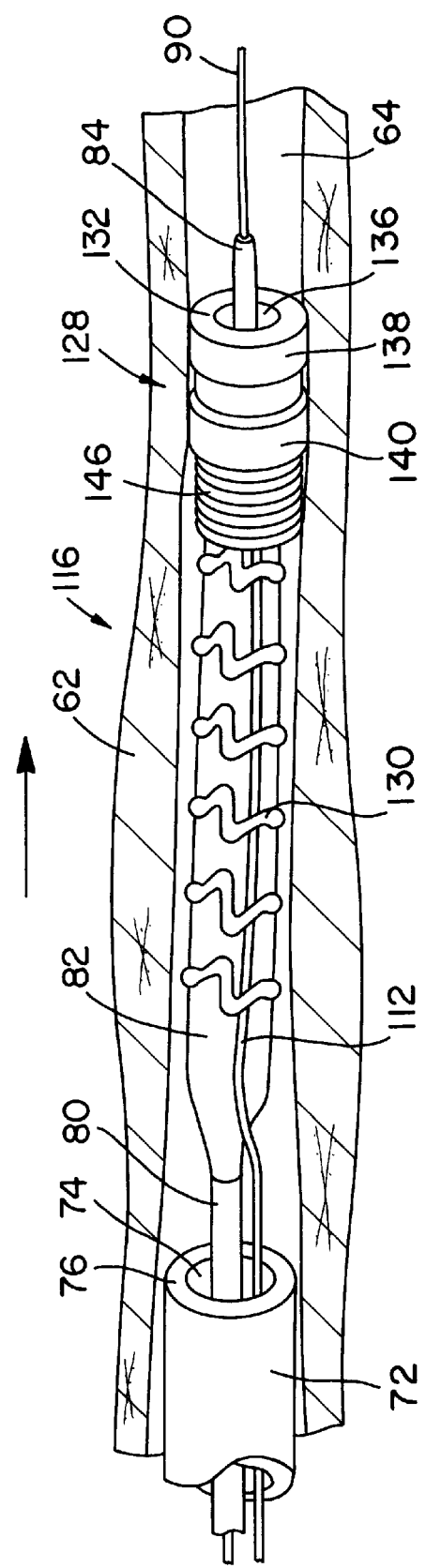

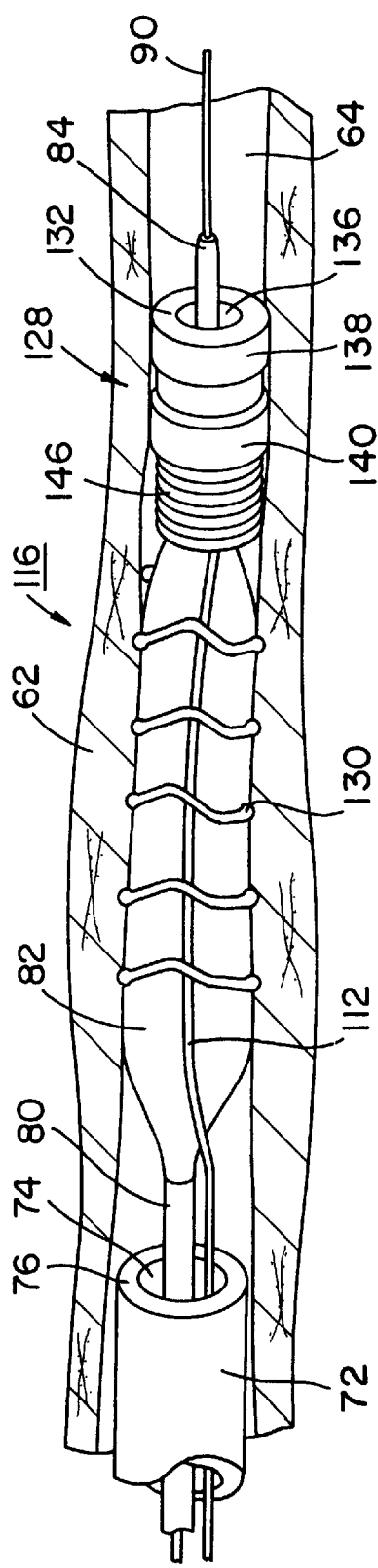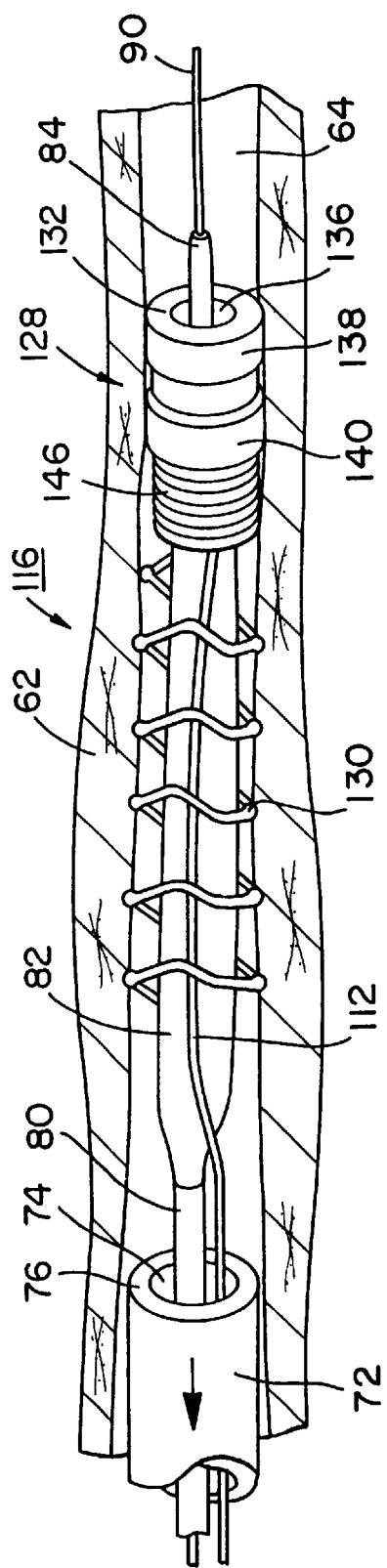

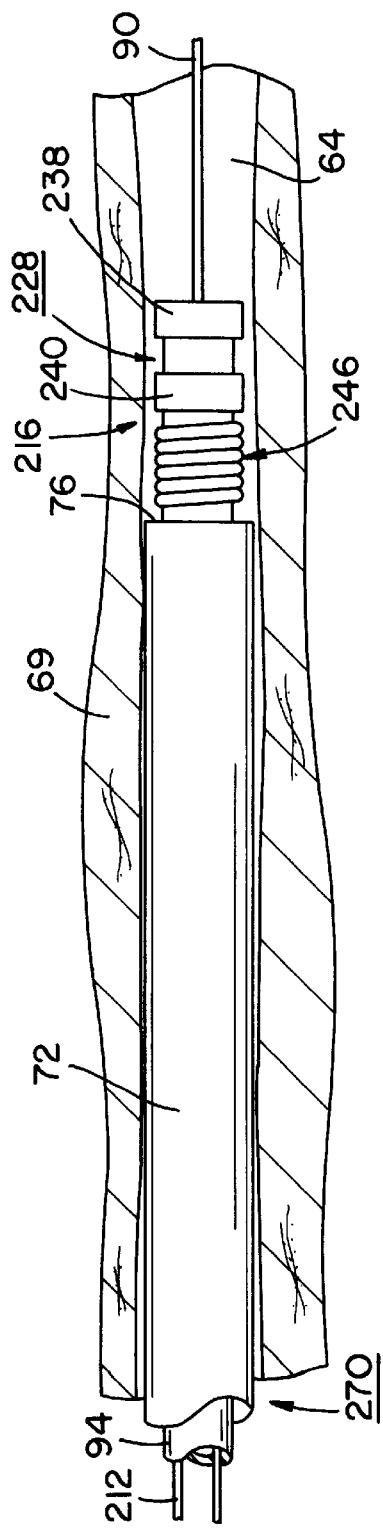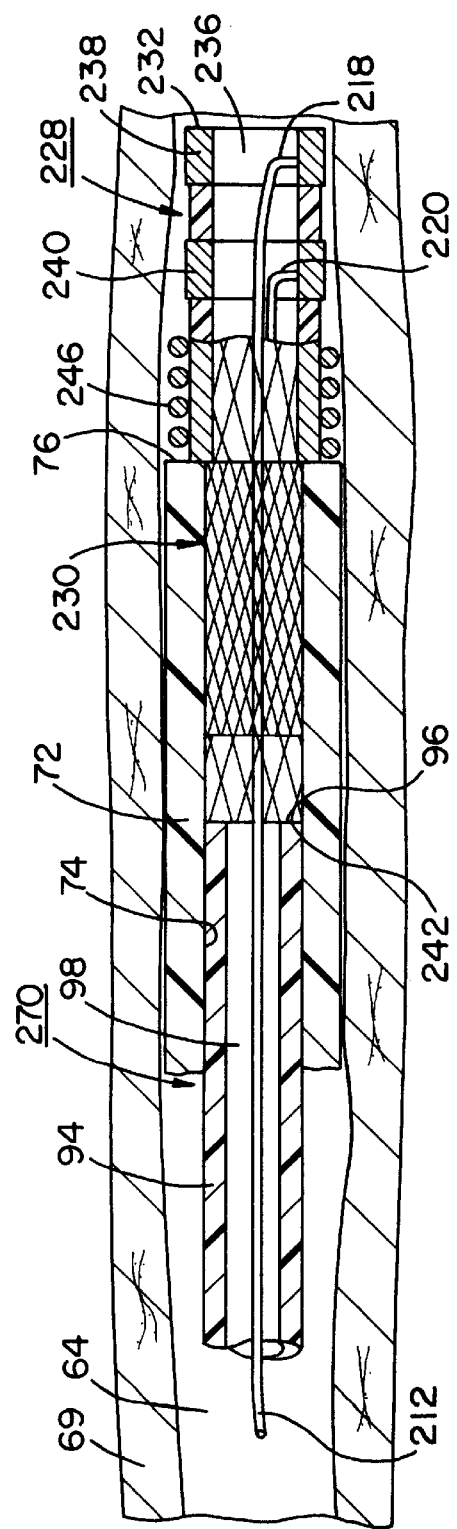

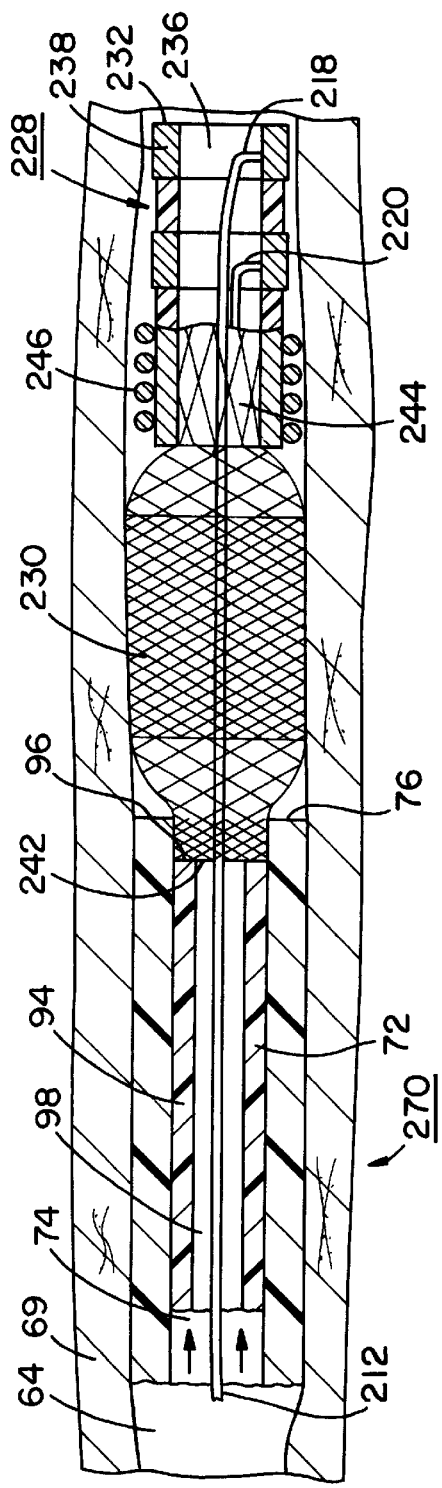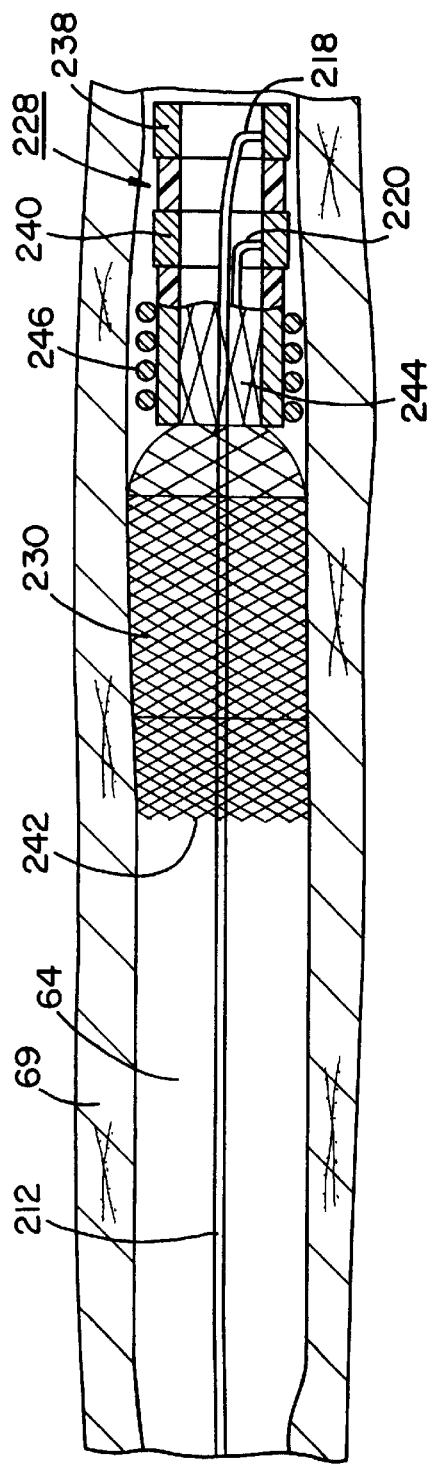

APPARATUS AND METHOD FOR FIXING ELECTRODES IN A BLOOD VESSEL

FIELD OF THE INVENTION

The present invention relates to endocardial implantable cardiac leads for applying electrical stimulation to and/or sensing electrical activity of the heart at one or more electrode positioned at a cardiac implantation site within a cardiac blood vessel adjacent a heart chamber and more particularly to such a lead particularly adapted to be implanted in the coronary sinus to maintain pace/sense electrodes at a desired orientation to the left ventricle or atrium of the heart.

BACKGROUND OF THE INVENTION

Implantable medical electrical stimulation and/or sensing leads are well known in the fields of cardiac stimulation and monitoring, including cardiac pacing and cardioversion/defibrillation, and in other fields of electrical stimulation or monitoring of electrical signals or other physiologic parameters of the body. A pacemaker or cardioverter/defibrillator implantable pulse generator (IPG) or a cardiac monitor is typically coupled to the heart through one or more of such endocardial leads. The proximal end of such leads typically is formed with a connector which connects to a terminal of the IPG or monitor. The lead body typically comprises one or more insulated, conductive wire surrounded by an insulating outer sleeve. Each conductive wire couples a proximal lead connector element with a distal stimulation and/or sensing electrode. An endocardial cardiac lead having a single stimulation and/or sensing electrode at the distal lead end and a single conductive wire is referred to as a unipolar lead. An endocardial cardiac lead having two or more stimulation and/or sensing electrodes at the distal lead end and two or more conductive wires is referred to as a bipolar lead or a multi-polar lead, respectively.

In order to implant an endocardial lead within a heart chamber, a transvenous approach is utilized wherein the lead is inserted into and passed through a pathway comprising the subclavian, jugular, or cephalic vein and through the superior vena cava into the right atrium or ventricle. It is necessary to accurately position the sense and/or stimulation electrode surface against the endocardium or within the myocardium at the desired site in order to achieve reliable sensing of the cardiac electrogram and/or to apply stimulation that effectively paces or cardioverts the heart chamber. The desired heart sites include the right atrium, typically the right atrial appendage, the right ventricle, typically the ventricular apex, and the coronary sinus and great vein descending therefrom.

The heart beats approximately 100,000 times per day or over 30 million times a year, and each beat stresses at least the distal portion of the lead. Over the years of implantation, the lead conductors and insulation are subjected to cumulative mechanical stresses, as well as material reactions as described below, that can result in degradation of the insulation or fractures of the lead conductors with untoward effects on device performance and patient well being. The endocardial lead body is subjected to continuous stretching and flexing as the heart contracts and relaxes and is formed to be highly flexible and durable. It is necessary to temporarily stiffen the lead body while advancing it through the pathway to locate the distal electrode(s) at the desired site.

Early implantable, endocardial and epicardial, bipolar cardiac pacing leads employed separate coiled wire conductors in a side by side configuration in the lead body and incorporated a lumen for receiving a stiffening stylet inside the lumen of at least one of the conductor coils to facilitate implantation. The stiffening stylet was advanced through a proximal connector pin opening to stiffen the lead body during the transvenous introduction and location of the distal electrodes deeply inserted into the right ventricular apex and was then withdrawn. The relatively large diameter and stiff lead body provided column strength that was relied upon to maintain the distal electrodes embedded into the trabeculae of the right ventricular apex. Fibrous tissue growth about the distal lead body was also relied upon to hold the distal pace/sense electrodes in position. Similar atrial, J-shaped lead bodies were developed that relied upon the lead body stiffness and shape to lodge and maintain distal pace/sense electrodes lodged into the right atrial appendage.

Such relatively large and stiff lead bodies were disadvantageous in a number of respects. The large diameter body made it difficult to implant more than one lead through the venous system. The column strength of such relatively large and stiff lead bodies often was insufficient to maintain the pace/sense electrodes in the atrial appendage or ventricular apex, and physicians often resorted to leaving the stylets in place, resulting in fracture of the lead bodies. Once the lead bodies fibrosed in, they were difficult to retract from the heart if they needed to be replaced. Thus, efforts were undertaken to solve all of these problems.

Considerable effort has been expended over the years to develop passive and active fixation mechanisms that are incorporated into the distal end of the endocardial lead to fix the electrode at a desired site in a heart chamber during an acute postoperative phase wile fibrous tissue growth tends to envelop the lead body. Passive fixation mechanisms do not invade the myocardium but cooperate with cardiac tissue or structures to locate the electrode or electrodes in contact with the endocardium. The most successful passive fixation mechanism comprises a plurality of soft, pliant tines that bear against cardiac structure surfaces, e.g. the trabeculae in the right ventricle and the atrial appendage, to urge the distal tip electrode against the endocardium. Active fixation mechanisms are designed to penetrate the endocardial surface and lodge in the myocardium without perforating through the epicardium or into an adjoining chamber. The most widely used active fixation mechanism employs a sharpened helix, which typically also constitutes the distal tip electrode. A shroud or retraction mechanism is provided to shield the helix during the transvenous advancement into the desired heart chamber from which the helix can be advanced and rotated when the desired site is reached to effect a penetrating, screw-in fixation. In one manner or another, the helix is adapted to be rotated by some means from the proximal end of the lead outside the body in order to screw the helix into the myocardium and permanently fix the electrode at the desired atrial or ventricular site.

Lead body design has progressed significantly over the years in the effort to increase longevity and flexibility and to diminish lead body size, while maintaining pull out strength to enable retraction of the lead body from the heart and increasing the number of conductors to distal electrodes or sensors. Co-axial, bipolar, coil lead bodies, of the type shown in U.S. Pat. No. 3,788,329, incorporated herein by reference, are widely used, wherein the separate coiled wire conductors are wound in differing diameters separated from one another by tubular insulating sheaths and extend coaxially about a central lumen for receiving the stiffening stylet. More recently, each such coiled wire conductor of both unipolar and bipolar leads is formed of a plurality of multi-filar, parallel-wound, coiled wire conductors electrically connected in common in an electrically redundant fashion. Such redundant coiled wire conductors of bipolar and multi-polar lead bodies are coaxially arranged about the stiffening stylet receiving lumen and insulated from one another by coaxially arranged insulating sheaths separating each coiled wire conductor from the adjacent coiled wire conductor(s).

In the implantation of a cardiac device of the types listed above, and in the replacement of previously implanted cardiac leads, two or more transvenous cardiac leads are typically introduced through the venous system into the right chambers or coronary sinus of the heart. It has long been desired to minimize the diameter of the transvenous cardiac lead body to facilitate the introduction of several cardiac leads by the same transvenous approach. Moreover, a number of multi-polar, endocardial cardiac leads have been designed to accommodate more than two electrodes or to make electrical connection with other components, e.g., blood pressure sensors, temperature sensors, pH sensors, or the like, in the distal portion of the lead. The increased number of separate polarity coiled wire conductors is difficult to accommodate in the conventional coaxial coiled wire conductor winding arrangement employing tubular insulating sheaths to separate the coil wire conductors of differing diameters having a desired overall lead body outer diameter.

These needs have led to the development of separately insulated, coiled wire conductors that are parallel-wound with a common diameter and are separately coupled between a proximal connector element and to a distal electrode or terminal in the manner described in commonly assigned U.S. Pat. No. 5,007,435, for example. The coaxial construction technique may also be combined with the parallel-winding technique to multiply the total number of separate coiled wire conductors accommodated within a specified endocardial lead body outer diameter.

All of the above considerations as to the complexity of the leads, the number of leads implanted in a common path, and the advancement of coronary sinus leads deep in the coronary veins have led to efforts to at least not increase and optimally to decrease the overall diameter of the cardiac lead body without sacrificing reliability and usability. It has been proposed to diminish the lead body further by eliminating the lumen for receiving the stiffening stylet and by replacing the coiled wire conductor with highly conductive stranded filament wires or cables. In bipolar or multi-polar leads, each such cable extends through a separate lumen of the lead body to maintain electrical isolation. Without the ability to use the stiffening stylet, it is necessary to resort to use of another mechanism to pass the lead through the vessel paths identified above and to position and fix the distal electrode of the lead at the desired site in the heart chamber or vessel. Moreover, the decreased lead body diameter and increased lead body flexibility reduces the column strength of the lead body and necessitates use of an active or passive fixation mechanism. Commonly assigned U.S. Pat. No. 5,246,014, incorporated herein by reference, presents a number of alternative designs of such straight, stranded filament wires used in small diameter lead bodies having an active fixation, distal tip electrode. An introducer surrounding the lead body, rather than a stiffening stylet in a lead body lumen, and engaging the distal active fixation mechanism is used to introduce and fix he electrode at the desired site.

A large number of endocardial pacing and cardioversion/defibrillation leads have also been developed that are adapted to be advanced into the coronary sinus and coronary veins branching therefrom in order to locate the distal electrode(s) adjacent to the left ventricle or the left atrium.

The distal ends of such coronary sinus leads are advanced through the superior vena cava, the right atrium, the valve of the coronary sinus, the coronary sinus, and into a coronary vein communicating with the coronary sinus, such as the great vein. Typically, coronary sinus leads that have been released for clinical use and bearing relatively small, ring-shaped pace/sense electrodes and/or larger, elongated, cardioversion/defibrillation electrodes have straight lead bodies and electrodes. Moreover, they do not employ any fixation mechanism and instead rely on the close confinement within these vessels and the column strength of the lead body extending back to the IPG or cardiac monitor to maintain each such electrode at a desired site. Such a cardioversion/defibrillation coronary sinus lead is disclosed in commonly assigned U.S. Pat. No. 5,174,288, incorporated herein by reference.

A number of considerations are important in the design of coronary sinus leads. It is desirable to avoid completely obstructing the coronary sinus and veins extending therefrom the vein, and therefore it is not desirable to encourage and rely upon tissue growth to stabilize the electrodes located therein. It is not desirable to damage or penetrate or perforate the vein wall which itself would contribute to tissue growth and obstruction. However, it is desirable to obtain and maintain a precise location of the electrode(s) so that they can be used to accurately sense electrical activity of the left atrium or ventricle and to apply localized electrical stimulation thereto.

These considerations have led to variations on coronary sinus lead body and electrode designs as disclosed in commonly assigned U.S. Pat. Nos. 5,170,802 and 5,224,491 and in further U.S. Pat. Nos. 5,387,233, 5,411,546, 5,423,865, and 5,476,498, all incorporated herein by reference. These coronary sinus leads use the shape of the lead body or the distal electrode to lodge against and extend the coronary sinus or great vein wall to hold the distal lead end at the desired site in relation to the left atrium or ventricle.

The '491 patent discloses the use of a balloon expandable or a self expanding, distal, stent-like electrode that is expanded or released and expands in the coronary sinus in order to distribute the electrode surface area over a wide area and to hold the distal lead end in place. A similar stent-like, cardioversion/defibrillation electrode that is used in other cardiac vessels is disclosed in U.S. Pat. No. 5,531,779, incorporated herein by reference. In U.S. Pat. No. 5,221,261, incorporated herein by reference, a number of embodiments of a stent retention mechanism for a catheter that dispenses fluids through a catheter body lumen are disclosed. It is suggested in regard to the first embodiment that the catheter body distal end can bear an electrode that is electrically connected to a conductor extending through the catheter lumen. Upon expansion of the stent retention mechanism, the catheter distal end is located centrally within the vessel lumen and separated from the vessel wall. This provides an inadequate electrode location for cardiac sense electrodes that are best applied directly against cardiac tissue. Moreover, blood flows around the periphery of the tip electrode rather than through a lumen of the distal electrode.

SUMMARY OF THE INVENTION

It is therefore an object of the present invention to provide an improved cardiac lead and retention mechanism adapted to be disposed in a blood vessel that allows substantially unimpeded blood flow through the blood vessel.

It is a further object of the invention to provide for the disposition of one or more small surface area electrode against a blood vessel wall while allowing substantially unimpeded blood flow centrally past the electrode(s).

These and other objects of the invention are realized in an arrangement to facilitate the disposition and retention of one or more distal electrode of a lead disposed on an electrode bearing structure against the wall of a body vessel through expansion of a stent retention mechanism (herein "stent" or "retention stent") extending axially from one end of the electrode bearing structure to place the electrode in contact with the body vessel wall and to allow body fluid to flow through the aligned lumen of the stent retention mechanism and a lumen of the electrode bearing structure. The invention is preferably realized and implemented in endocardial leads for locating and fixing one or more sensing and stimulation electrode against a cardiac blood vessel wall while allowing blood flow through the axially aligned lumens of the stent retention mechanism and electrode bearing structure The endocardial leads of the present invention includes a lead body extending between a proximal lead end and a distal lead end, at least one lead conductor extending within the lead body between the proximal and distal lead ends, and at least one cardiac electrode at or adjacent the distal lead end electrically conducted to the lead conductor and a distal, expandable stent. The distal electrode(s) is supported by a tubular electrode support having a diameter large enough to bear against the blood vessel wall and a support lumen that allows blood to flow through it. The stent extends proximally from a distal stent end fixed to the tubular electrode support to a proximal stent end. The stent is expandable from a collapsed stent state to an expanded stent state providing an expanded stent lumen that is aligned with the electrode support lumen for allowing blood to flow through the aligned electrode support lumen and expanded stent lumen.

Generally, the retention stent is expandable from the collapsed stent state in which the outer diameter of the retention stent is less than the inner diameter of the vessel to an expanded stent state having an increased outer diameter. In the expanded stent state, the stent lumen has an expanded stent lumen diameter approximately equal to or exceeding the inner diameter of the vessel lumen sufficiently to lodge the stent against the blood vessel wall and inhibit movement of the stent and distal electrode support.

The lead body preferably comprises a small diameter lead body extending proximally from the distal lead end coupled with the distal electrode(s) and proximally through the stent lumen to the proximal lead end. The distal electrode support, the retention stent and the lead body are supported by a lead delivery mechanism during transvenous introduction to the cardiac implantation site, and the delivery mechanism is withdrawn when the retention stent is deployed.

Preferably, the delivery mechanism comprises an introducer, the retention stent and lead body are enclosed within the introducer lumen or mounted to the exterior surface of the introducer, and the tubular distal electrode support extends distally from the introducer distal end during introduction. The retention stent may take any of the known forms that can be introduced in the collapsed stent state within the introducer lumen and assume the expanded stent state at the desired cardiac implantation site of fixation of the electrode(s) against the blood vessel wall. The retention stent may either be self-expanding upon release in the blood vessel or be mechanically expanded within the blood vessel.

In the former case, the stent is preferably mechanically restrained to the collapsed stent state diameter during introduction and released from the mechanical restraint to expand to the expanded stent state stent diameter. The mechanical restraint can be effected by the lead delivery introducer, and the release can be effected by simply pushing the compressed retention stent out of the introducer lumen. Alternatively, the retention stent can be restrained on the outer surface of a delivery catheter in a collapsed stent state and released therefrom to expand to the expanded stent state. The retention stent may be formed of a material that undergoes a pseudoelastic deformation upon release from restraint.

In the latter case, the delivery mechanism further comprises a miniaturized balloon catheter for delivering the retention stent and mechanically expanding it from the collapsed stent state to the expanded stent state. A stent expansion balloon at the distal end of the balloon catheter is extended through the stent lumen and supports the retention stent in the collapsed stent state within the introducer lumen during transvenous introduction. The balloon and stent are advanced out of the introducer catheter lumen at the desired cardiac implantation site in the blood vessel, and the balloon is expanded to expand the retention stent to the expanded stent state diameter and against the blood vessel wall. Then, the balloon is deflated, and the balloon catheter and introducer are withdrawn.

Preferably, two electrodes are disposed at distal and proximal locations on the outer surface of the distal electrode support and are spaced apart from one another by a close fixed spacing that provides a bipolar, near field sensing axis or dipole for sensing the near field electrogram of the heart chamber that the electrodes are disposed toward in use. The electrodes can be formed as ring-shaped surface electrodes extending around the circumference of the tubular distal electrode support or as arcuate-shaped surface electrodes disposed side by side axial alignment along the tubular distal electrode support. In the latter case, the distal electrode support and attached retention stent are rotated within the blood vessel by rotation of the delivery mechanism to orient align the sensing dipole to the desired heart chamber.

In use as coronary sinus endocardial leads, the electrode support and retention stent are preferably disposed in the coronary sinus to locate the sensing dipole close to the left or right atrium or deeper into the great vein that branches from the coronary sinus to locate the sensing dipole close to the left ventricle. The distal electrodes are fixed in direct contact with the blood vessel wall for optimal sensing.

The endocardial leads of the present invention are preferably employed with implantable monitors for monitoring the cardiac EGM or with pacemaker IPGs for pacing the heart by delivery of pacing pulses to the electrode(s).

The lead body is preferably highly miniaturized in diameter to avoid obstructing blood flow through the aligned retention stent lumen and distal electrode support lumen and so flexible that it does not have appreciable column strength. The arrangement of the present invention advantageously provides a simplified apparatus for and method of introducing endocardial cardiac leads which lack a lumen for receiving a stiffening stylet and lack sufficient column strength to be pushed to a desired cardiac implantation site and fixing the distal lead end at the desired cardiac implantation site in a cardiac blood vessel.

This summary of the invention and the objects, advantages and features thereof have been presented here simply to point out some of the ways that the invention overcomes difficulties presented in the prior art and to distinguish the invention from the prior art in one or more independent way and is not intended to operate in any manner as a limitation on the interpretation of claims that are presented initially in the patent application and that are ultimately granted.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIGS. 4–8 are schematic depictions of the assembly of the lead with the lead delivery mechanism and steps of delivering the distal lead end and expanding the retention stent in a cardiac implantation site, e.g., the coronary sinus as depicted in FIG. 3;

FIGS. 10–13 are schematic depictions of the assembly of the lead with the delivery mechanism and steps of delivering the distal lead end and expanding the retention stent in a cardiac implantation site, e.g., the great vein as depicted in FIG. 9.

DETAILED DESCRIPTION OF THE PREFERRED EMBODIMENTS OF THE INVENTION

Figure 1:
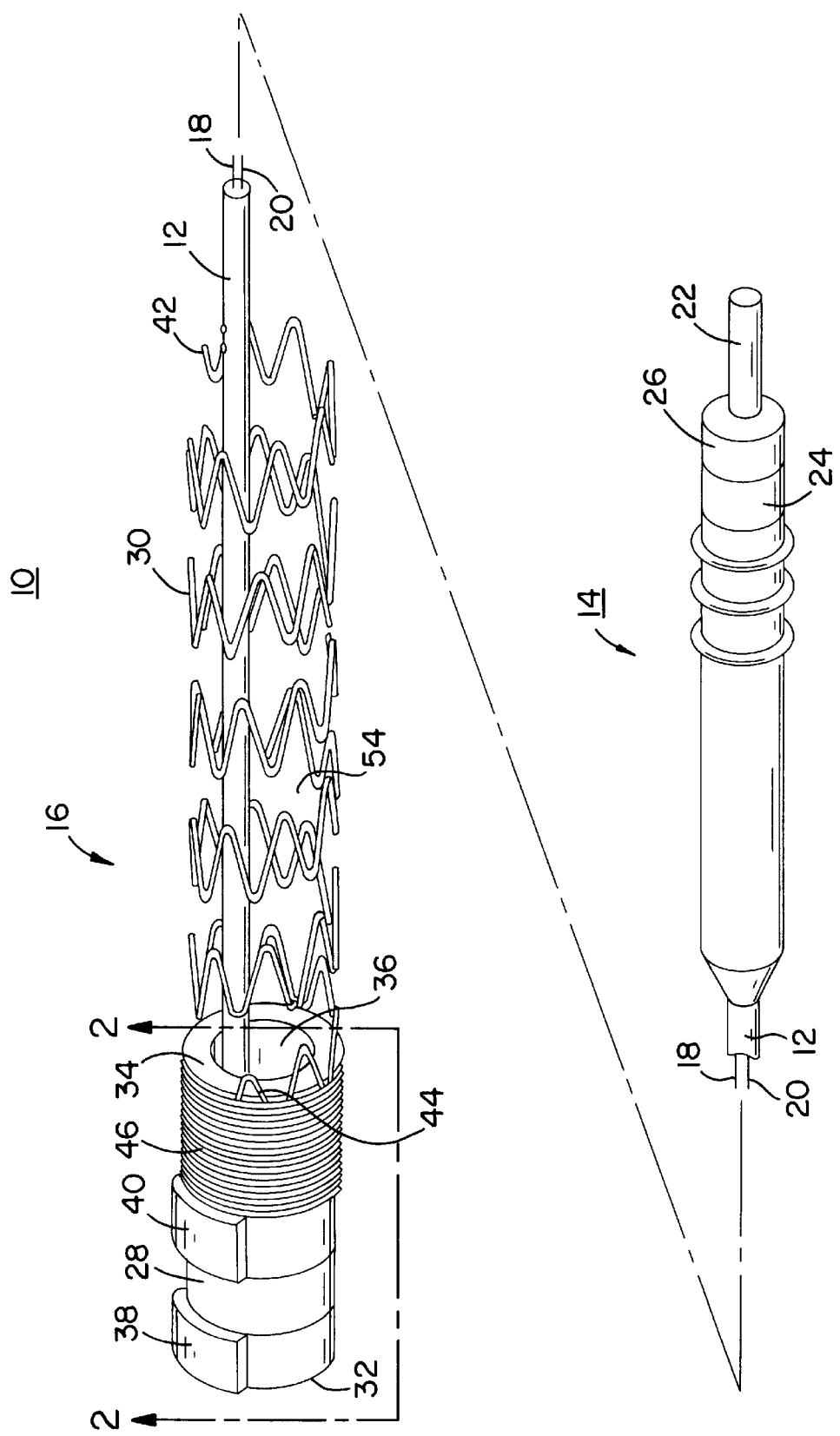
FIG. 1 is a perspective view of a cardiac lead in accordance with one embodiment of the invention.

In the following detailed description, references are made to illustrative embodiments endocardial leads adapted to be located in cardiac blood vessels for carrying out the invention. It is understood that the invention may be practiced in respect to other body implantable leads located in elongated body lumens of body organs, ducts or tracts where body fluid flows.

The invention and its preferred embodiment may be implemented in unipolar, bipolar or multi-polar, endocardial, cardiac pacing and/or sensing leads having one or more pace/sense electrode(s) or sense electrode(s), respectively, at or adjacent the distal lead end. Similarly, the invention and its preferred embodiments may be implemented in endocardial cardiac defibrillation/cardioversion leads including at least one cardioversion/defibrillation electrode and optionally including one or more pace/sense electrode(s) at or adjacent the distal lead end. Moreover, other sensors for sensing a physiologic parameter may be incorporated into the lead body. Each such pace/sense electrode, sense electrode, cardioversion/defibrillation electrode and sensor is coupled with an insulated electrical conductor extending proximally through the lead body to a proximal lead end connector assembly. The proximal connector end assembly is adapted to be coupled to the connector assembly of an implantable or external medical device, including an external pulse generator or an IPG for pacing, cardioversion/defibrillation or both or an external or implantable monitor. Therefore, it will be understood that the arrangement for introduction of an endocardial cardiac lead of the present invention can be employed to introduce permanently implantable and temporary cardiac leads of these types.

The arrangement of the present invention is particularly useful in introducing such endocardial cardiac leads which are quite small in lead body diameter and are so flexible and possess such low column strength that the distal lead end cannot be advanced transvenously and positioned at the desired implantation site without assistance. Moreover, one particular use of the arrangement of the present invention is to introduce and fix such endocardial cardiac leads that are formed using stranded wire conductor(s) of the type described in the above-incorporated, commonly assigned, '014 patent. The lead body outer diameter is minimized by use of such conductors and by eliminating the lumen for receiving a stiffening stylet.

All of the embodiments of the invention include such a lead body extending between a proximal lead end and a distal lead end, at least one lead conductor extending within the lead body between the proximal and distal lead ends, and at least one cardiac electrode at or adjacent the distal lead end electrically conducted to the lead conductor and a distal retention stent that is expanded at the cardiac implantation site. The distal electrode(s) is supported by a tubular electrode support having a diameter large enough to bear against the blood vessel wall and a support lumen that allows blood to flow through it. In the illustrated embodiments, the retention stent extends proximally from a distal stent end fixed to the tubular electrode support to a proximal stent end. However, it will be understood that the retention stent could be alternatively be supported at and extend distally from the distal end of the tubular electrode support.

The retention stent is expandable from a collapsed stent state to an expanded stent state providing an expanded stent lumen that is aligned with the electrode support lumen for allowing blood to flow through the aligned electrode support lumen and expanded stent lumen.

FIG. 1 illustrates such a bipolar cardiac lead 10 in accordance with one embodiment of the invention and includes a lead body 12 extending between a proximal lead end 14 and a distal lead end 16. The distal lead end 16 comprises a tubular, distal electrode support 28 that supports a retention stent 30 that is attached to and extends proximally from the electrode support 28 and surrounds lead body 12. Distal electrode support 28 also supports and electrically isolates distal electrode 38 from proximal electrode 40 and from the stent.

The lead body 12 encloses a pair of lead conductors 18 and 20 that extend within the lead body 12 between the proximal lead end 14 and distal lead end 16 formed and dimensioned as described above. The distal ends of lead conductors 18 and 20 are coupled to the distal and proximal electrodes 38 and 40, respectively. The proximal lead end 14 is configured as a conventional in-line bipolar connector body 26 comprising a connector pin 22 coupled with the proximal end of lead conductor 18 and a connector ring 24 coupled with the proximal end of lead conductor 20. The connector body 26 is adapted to fit into a connector receptacle of an implantable monitor or pacemaker IPG in a manner well known in the art.

Figure 2:
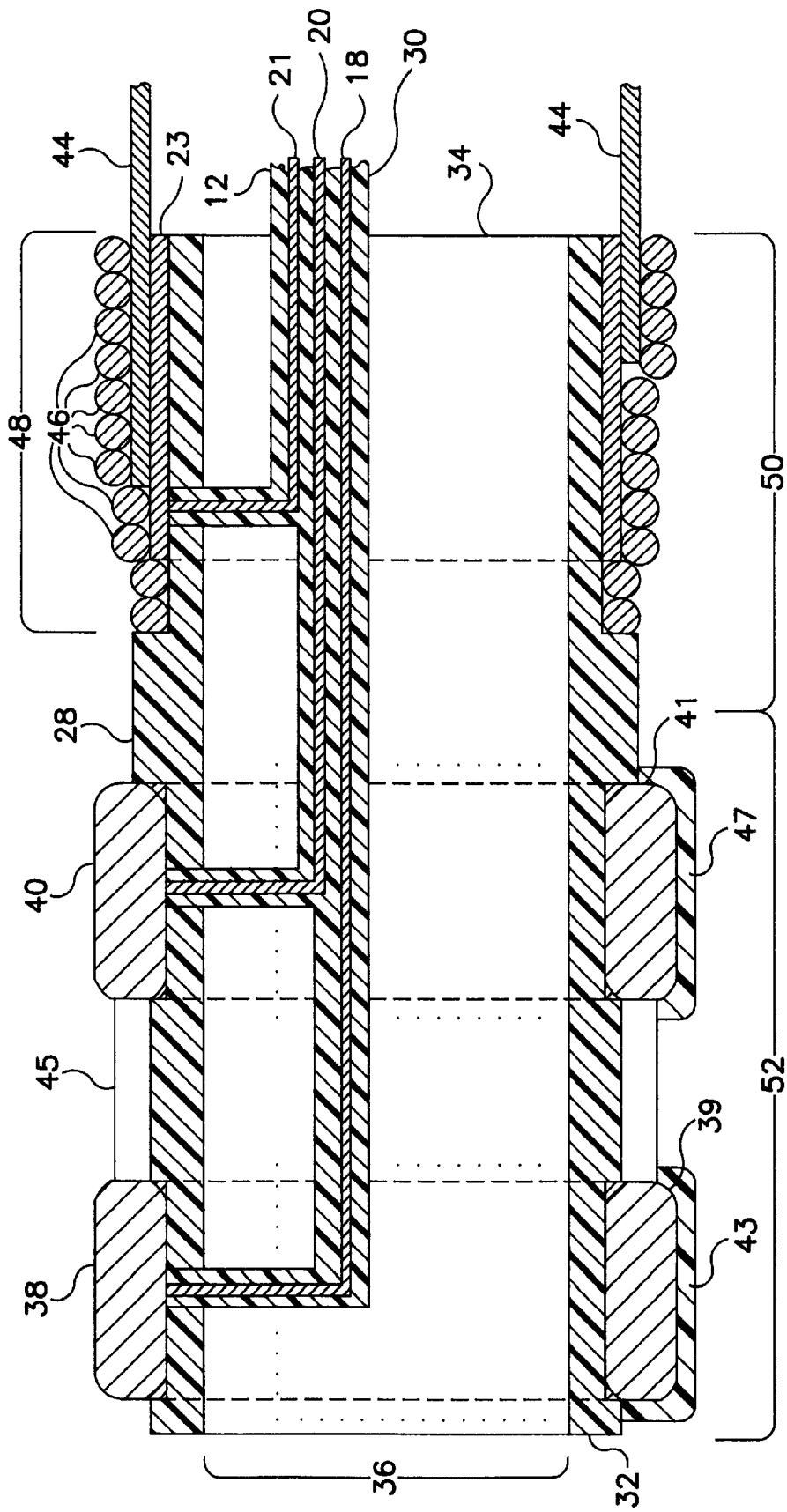
FIG. 2 is a cross-section view taken along section lines 2—2 of FIG. 1 schematically depicting the construction of the tubular distal electrode support and its attachment with the lead body distal end and the retention stent distal end.

While the lead 10 of FIG. 1 is depicted as a bipolar lead, the invention may be practiced in a unipolar lead employing only the distal electrode 38. However, the lead body 12 could include a further lead conductor that is coupled at its distal end to the distal end 44 of the retention stent 30 to use the stent 30 as an indifferent electrode or to provide a tri-polar sense electrode. Moreover, the distal electrode 38 and proximal electrode 40 may be formed in many shapes, e.g., a full ring shape or as a ring segment shape. FIG. 2 illustrates these alternative optional features in combination that may be selectively eliminated or altered in devising a particular lead are depicted in FIG. 2.

In FIG. 2, tubular, single piece, distal electrode support 28 is formed with a through lumen 36 and extends between distal and proximal support lumen end openings at the respective distal and proximal electrode support ends 32 and 34. Distal electrode support 28 is either formed of a biocompatible non-conductive material or conductive material coated by a non-conductive material to support and electrically isolate distal electrode 38 from proximal electrode 40 and from the stent distal end 44. The tubular distal electrode support 28 supports a distal conductive ring 39 and a proximal conductive ring 41 at spaced apart, annular recesses on the outer surface of a distal support section 52 and supports the retention stent proximal end 44 on the outer surface of a proximal support section 50.

In the depicted electrode shape embodiment, thin, electrically insulating, electrode coatings 43 and 47, e.g., a Parylene™ polymer, cover most of the exposed surfaces of conductive rings 39 and 41. The distal and proximal electrodes 38 and 40 are thereby formed of asymmetric, arcuate or ring segment shape portions of conductive rings 39 and 41 that are exposed. In this way, the distal and proximal electrodes 38 and 40 are axially spaced from one another in the distal support section 52 along one side of the tubular distal electrode support 28. Alternatively, other segments or the entire outer surface of conductive rings 39 and 41 can be left exposed all the way around the circumference of the tubular distal electrode support 28 to function as the distal and proximal electrodes 38 and 40, respectively.

Distal electrode 38 and proximal electrode 40 are coupled with the distal ends of the lead conductors 18 and 20, respectively, of lead body 12 which extends proximally through the electrode support lumen 36 as shown in FIG. 2. It will be understood that the distal and proximal conductive rings 39 and 41 and the connections with the distal ends of lead conductors 18 and 20 are depicted schematically. The electrodes 38 and 40 can be formed in a variety of other ways. The distal and proximal conductive rings 39 and 41 can be formed with connector elements formed on their inner surfaces extending into the lumen 36 to receive the distal ends of lead conductors 18 and 20 in a variety of ways.

It is also preferred to incorporate a monolithic controlled release device (MCRD) 45 that constitutes a steroid eluting polymer material in a manner well known in the art into the distal end 16. In FIG. 2, the MCRD 45 is formed in a band extending around the tubular distal electrode support 28 between the conductive rings 39 and 41.

The retention stent 30 is generally tubular and extends from proximal stent end 42 to a distal stent end 44 and defines a stent lumen 54 extending between the proximal and distal stent ends 42 and 44 through which the lead body 12 extends. The illustrated retention stent 30 is preferably formed of a wire bent in zigzag pattern. The retention stent 30 is depicted in the expanded stent state wherein the stent lumen 54 and the distal electrode support lumen 36 are approximately the same in diameter. The distal stent end 44 is secured around the outer surface of the proximal section 50 of tubular distal electrode support 28. This retention stent 30 can be expanded from a compressed stent state to the depicted expanded stent state either by use of an expansion mechanism or can self expand when released from a compressed stent state upon delivery to and release at a cardiac implantation site in a blood vessel so that the expanded stent 30 and the distal and proximal electrodes 38 and 40 engage the vessel wall.

A retention coil 46 is wrapped around the annular, exterior recess 48 of proximal portion 50 and overlies and compresses the distal stent end 44 against the exterior recess 48. The retention coil 46 is preferably formed of round or square wire formed of a noble metal, e.g., platinum, for strength and bio-compatibility.

Optionally, the distal stent 30 can be employed as a further electrode that is coupled to a further lead conductor 21 within lead body 12. A conductive coupling ring 23 is first placed in the annular, exterior recess 48 and attached to the distal end of the further lead conductor 21. The distal stent end 44 is fitted over the exterior surface of the conductive coupling ring, and the retention coil 46 is wrapped over it to compress the distal stent end 44 between the conductive wire turns of the retention coil 46 and the conductive coupling ring 23 making a secure electrical and mechanical connection therebetween.

In this way, the distal and proximal electrodes 38 and 40 are supported by a tubular electrode support 28 having a diameter large enough to bear against the blood vessel wall and a support lumen 36 that allows blood to flow through it and past the small diameter lead body 12. The retention stent 30 extending proximally from the distal stent end 44 fixed to the tubular electrode support 28 is expandable from a collapsed stent state to an expanded stent state providing the expanded stent lumen 54 that is aligned with the electrode support lumen 36 for allowing blood to flow through the aligned electrode support lumen 36 and expanded stent lumen 54.

In use, the retention stent 30 is expandable from the collapsed stent state in which the outer diameter of the retention stent 30 is less than the inner diameter of the vessel to an expanded stent state having an increased outer diameter. In the expanded stent state, the stent lumen 54 has an expanded stent lumen diameter approximately equal to or exceeding the inner diameter of the vessel lumen sufficiently to lodge the stent 30 against the blood vessel wall and inhibit movement of the stent 30 and distal electrode support 28. The distal electrode support 28, the retention stent 30 and the lead body 12 are supported by a delivery mechanism during transvenous introduction to the cardiac implantation site, and the delivery mechanism is withdrawn when the retention stent 30 is deployed and expanded.

Figure 3:
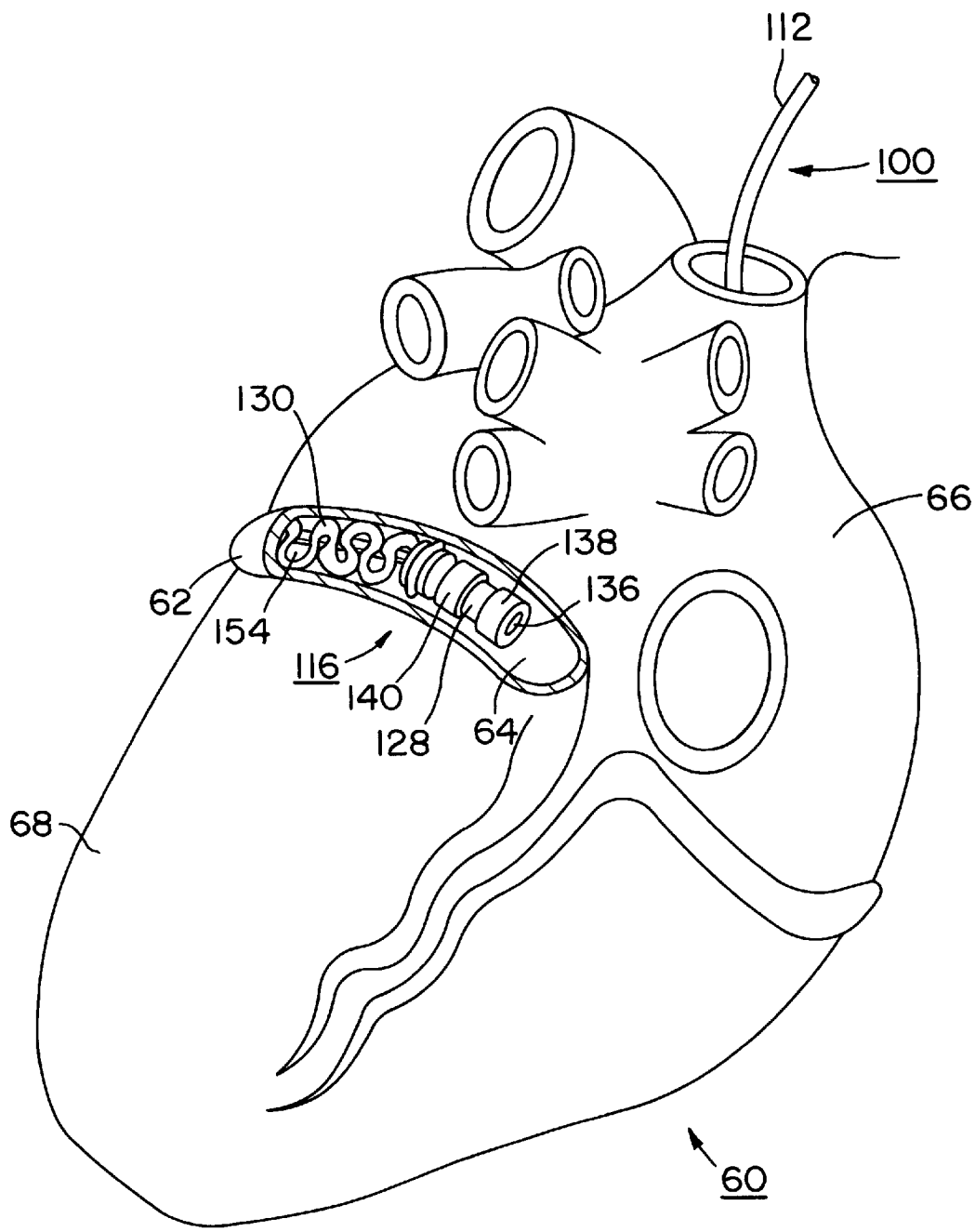
FIG. 3 is a schematic representation of the distal lead end of a coronary sinus endocardial cardiac lead in accordance with a further embodiment of the invention introduced into the coronary sinus adjacent the left heart chambers.

FIG. 3 shows a posterior view of the heart 60 with the external wall of the coronary sinus 62 cut open and schematically illustrates the location of the distal lead end 116 of a coronary sinus endocardial cardiac lead 100 introduced into the coronary sinus lumen 64 in accordance with a further embodiment of the invention. The distal lead end 116 comprises the tubular distal electrode support 128 and the proximally extending expandable retention stent 130. The ring-shaped distal and proximal electrodes 138 and 140 are disposed in the coronary sinus lumen 64 adjacent the left atrium 66 and left ventricle 68. The distal electrode support 128 is otherwise the same as distal electrode support 28 and is formed with a distal support lumen 136 that allows blood to flow therethrough. The retention stent 130 may take any of the known stent forms that can be introduced in the collapsed stent state within an introducer lumen 74 and assume the expanded stent state at the desired cardiac implantation site of fixation of the electrode(s) against the blood vessel wall. The distal lead end 116 is maintained in the coronary sinus lumen 64 by the expanded retention stent 130 which, in this illustrated embodiment, takes the form of an expandable intravascular stent of the type disclosed in U.S. Pat. No. 4,886,062, incorporated herein by reference. Retention stent 130 is attached to the proximal end of the retention stent 130 in the manner described above with reference to FIG. 2 and has a stent lumen 154 that the lead body 112 extends through and blood flows through.

FIGS. 4–8 are schematic depictions of the assembly of the lead delivery mechanism 70 with the lead 100 and the steps of delivering the distal lead end 116 and expanding the retention stent 130 in a cardiac implantation site, e.g., the coronary sinus lumen 64 as depicted in FIG. 3. In this embodiment, the delivery mechanism 70 comprises an introducer 72 and a balloon catheter 80 that engage the distal lead end 116 and are optionally introduced as an assembly over a guidewire 90 to the desired cardiac implantation site. However, it may be possible to simply advance the assembly to the desired cardiac implantation site without the use of a guidewire 90.

During introduction as illustrated in FIG. 4, the retention stent 130 and lead body 112 are enclosed within the introducer lumen 74, and the tubular distal electrode support 128 abuts the introducer distal end 76 and extends distally from the introducer distal end 76. The assembly may be rotated at the desired cardiac implantation site to a desired angular orientation of the distal and proximal electrodes 138 and 140 to the heart chamber if the electrodes 138 and 140 are shaped asymmetrically as in the embodiment of FIG. 1. If the guidewire 90 is used, it can be left in place or retracted after the assembly is advanced to the desired cardiac implantation site.

Figure 8:
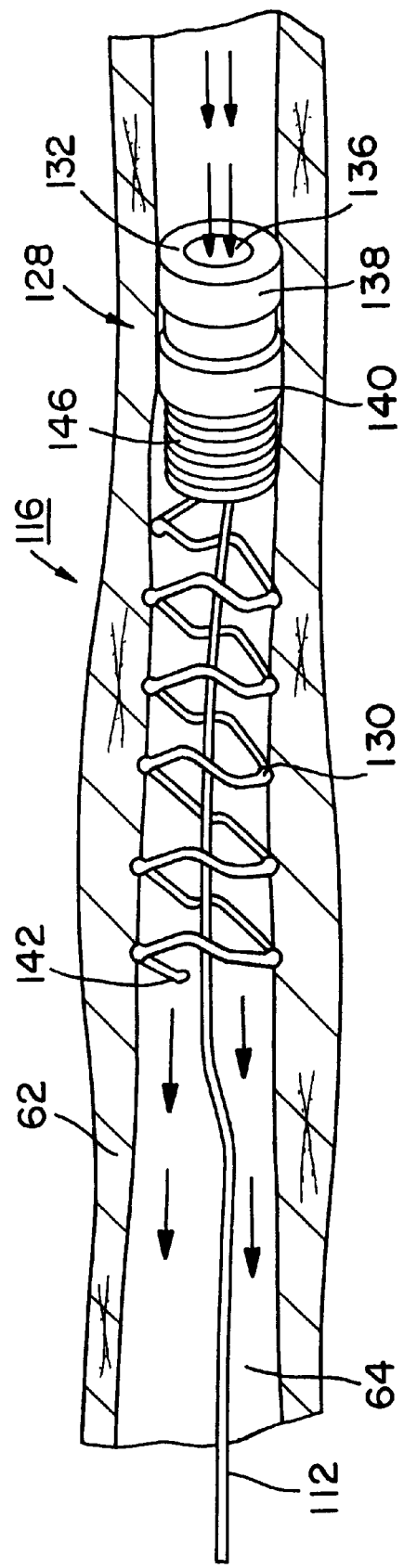

The miniaturized balloon catheter 80 is then used in conjunction with the introducer 70 for advancing the retention stent 130 out of the introducer lumen 74 as shown in FIG. 5. After it is ejected from the introducer lumen 74, the balloon 82 is expanded with fluid to mechanically expand the stent diameter from the collapsed stent state to the expanded stent state to engage against and slightly distend the blood vessel wall as shown in FIG. 6. Then, the balloon 82 is deflated as shown in FIG. 7, and the delivery mechanism 70 is withdrawn proximally over the lead body 112 leaving the distal lead end 116 deployed and stabilized at the desired cardiac implantation site as shown in FIG. 8. The guidewire 90 can then be withdrawn if it has been employed.

The configuration of the retention stent 130 is such that the wire of which it is formed is initially pre-formed into a two-dimensional zigzag form, and subsequently wrapped around a suitable mandrel to provide a hollow cylindrical structure having an external diameter less than the internal diameter of the blood vessel in which it is intended to be implanted as shown in FIG. 5. Expansion of the stent wire as shown in FIG. 6 to the expanded stent state causes some permanent deformation of the retention stent 130 by straightening of the zigzag bends. The expanded stent state allows the retention stent 130 to remain in contact with the coronary sinus wall after deflation of the balloon 82 and withdrawal of the delivery mechanism 70 as shown in FIG. 8.

It is necessary to assemble the distal lead end 116 with the lead delivery mechanism 70 prior to undertaking the implantation steps of FIGS. 4–8. During fabrication, the distal lead conductor ends are attached to the electrodes 138 and 140 in the manner described above with reference to FIG. 2. The stent 130 is formed in the collapsed stent state and the stent distal end is attached to the proximal end of the distal electrode support 128 using the retention coil 146, and the lead body is inserted through the retention stent lumen 154 in the manner described above with reference to FIG. 2.

Then, after assembly of the lead 100 is completed, it is necessary to mount the lead 100 with the lead delivery mechanism 70 to form the assembly suitable to be used in the manner depicted in FIGS. 4–8. One way of doing so involves the following steps. The proximal lead end is inserted through the distal end opening of the introducer lumen 74 and advanced proximally until it exits the introducer lumen proximal end opening. The balloon catheter 80 is advanced either proximally or distally through the introducer lumen 74 until the balloon 82 and balloon catheter distal end 84 are located adjacent to the distal lead end 116. The balloon catheter distal end 84 and the balloon 82 are inserted through the aligned stent lumen 154 and electrode support lumen 136 so that the assembly appears as shown in FIG. 5. The balloon catheter 80 and lead 100 are then retracted distally into the introducer lumen 74 to the initial position depicted in FIG. 4, and the steps of implantation illustrated in FIGS. 4–8 can be undertaken as described above.

This method of fabrication of the endocardial lead 100, assembly with the lead delivery mechanism 70 and implantation of FIGS. 4–8 can also be followed in the fabrication, assembly and implantation of the endocardial lead 10 depicted in FIG. 1. The expandable stent 130 can take many other different forms that can be flexibly coupled at one end to the electrode support proximal end. Such alternative expandable stent forms include the various embodiments of balloon expandable wire mesh stents, coiled wire stents, and solid tubular stents disclosed in U.S. Pat. Nos. 4,733,665, 5,078,726, and 5,242,451, all incorporated herein by reference. The stent material may constitute a shape memory alloy, e.g., Nitinol, and be introduced and expanded as described in the '451 patent, for example.

Figure 9:
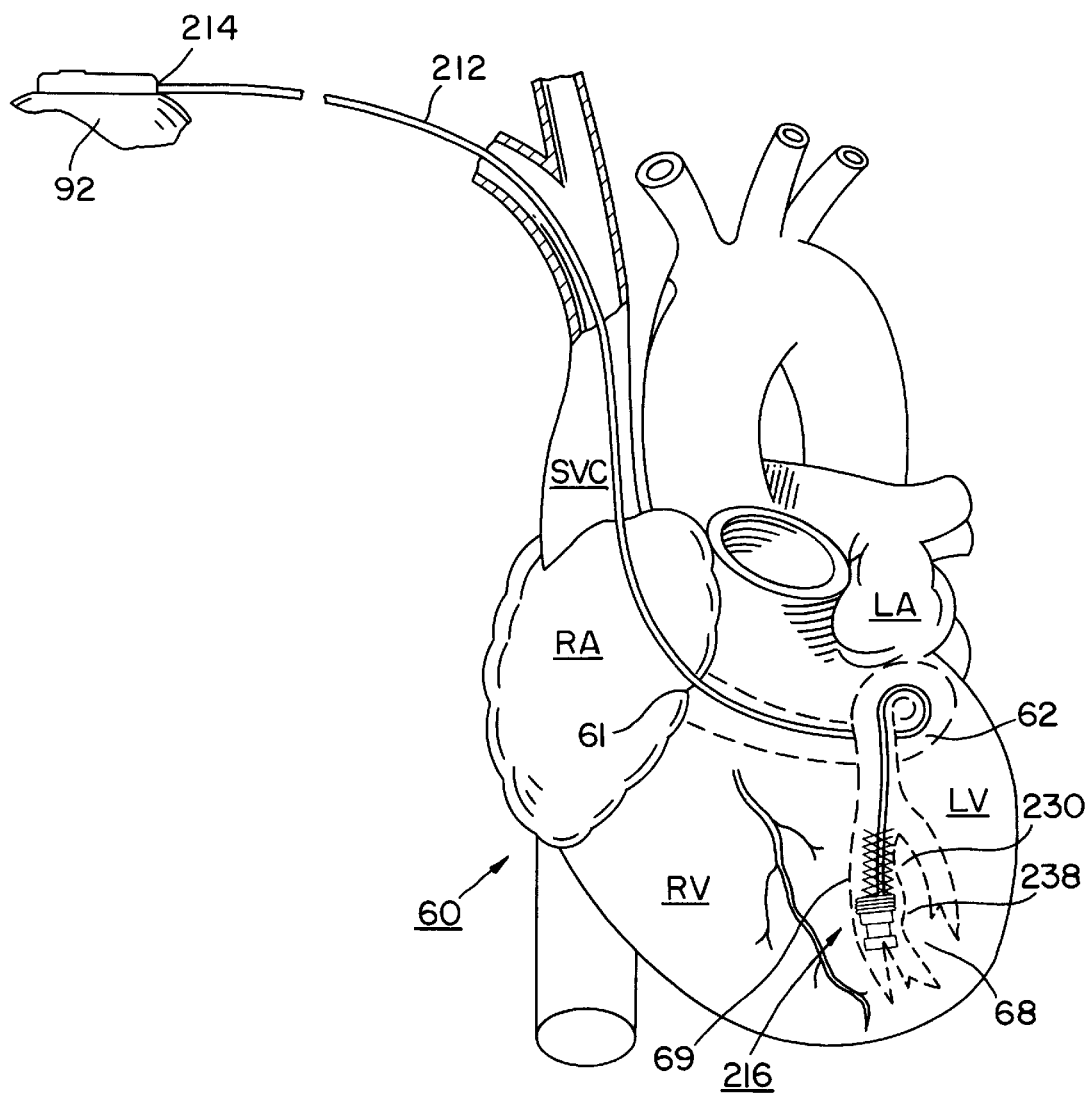
FIG. 9 is a schematic representation of the distal lead end of a coronary sinus endocardial cardiac lead in accordance with a still further embodiment of the invention introduced into the great vein descending from the coronary sinus adjacent the left ventricle.

FIG. 9 is a schematic representation of the distal lead end of a coronary sinus endocardial lead 200 constructed and introduced into the great vein 69 descending from the coronary sinus 62 adjacent the left ventricle 68 in accordance with a still further embodiment of the invention. In this view, the proximal lead connector end 214 is coupled to an implantable monitor or pacemaker IPG 92, and the lead body 212 extends in a typical transvenous pathway through the superior vena cava, the right atrium, the ostium 61, through the coronary sinus 62 and into the great vein 69 to locate the distal electrode(s) adjacent to the left ventricle. The proximal lead connector end is attached to the implantable monitor or pacemaker IPG 92 after expansion of the delivery stent 230 and withdrawal of the lead delivery mechanism. This route and attachment to an implantable monitor or pacemaker IPG 92 can also be followed in the implantation of the coronary sinus leads 10 and 100 described above.

This coronary sinus endocardial lead 200 is exemplary of such leads of the present invention that employ a self-expanding retention stent 230 that does not require externally applied force to expand it from the collapsed stent state to the expanded stent state. The retention stent 230 is coupled at only one stent end to the tubular electrode support 228 and therefore has a free open end when in the expanded stent state. The retention stent 230 is depicted and described hereafter as being in the form of a wire mesh of bent spring wires that are compressed to a compressed state diameter during delivery and expand by spring force into a larger diameter, tubular expanded stent state. Such self-expanding mesh stent structures that are ejected from an introducer lumen are disclosed, for example, in the above-incorporated '491 and '261 patents and in U.S. Pat. No. 5,064,435, incorporated herein by reference. However, it will be understood that the tubular self-expanding retention stent can take any other form such as spiral or mesh or solid stents that are supported in a collapsed stent state about the circumference of a delivery catheter as taught, for example, in U.S. Pat. Nos. 5,306,294 and 5,372,600, both incorporated herein by reference, and released to expand to the expanded stent diameter. The stent material can also constitute a shape memory alloy that expands in response to body temperature as disclosed in U.S. Pat. Nos. 4,553,545 and 5,037,427, both incorporated herein by reference.

FIGS. 10–13 are schematic depictions of the assembly of the lead delivery mechanism 270 with the lead 200 and the steps of delivering the distal lead end 216 and expanding the wire mesh retention stent 230 in a cardiac implantation site, e.g., the great vein 69 depicted in FIG. 9 or in the coronary sinus lumen 64 as depicted in FIG. 3. In this embodiment, the delivery mechanism 270 comprises the coaxial arrangement of introducer 72 and a pusher catheter 94 within the introducer lumen 74. The lead delivery mechanism 270 and the lead 200 are assembled as shown in FIGS. 10 and 11 in a manner analogous to that described above with reference to the embodiment of FIGS. 3–8. The assembly of the lead delivery mechanism 270 and lead 200 are optionally introduced over a guidewire 90 that is first advanced through the transvenous route to the desired cardiac implantation site as shown in FIG. 10. However, it may be possible to simply advance the assembly to the desired cardiac implantation site without the use of a guidewire 90 as shown in FIG. 11.

During introduction through the transvenous route as illustrated in FIGS. 10 and 11, the retention stent 230 is compressed into its compressed state and enclosed within a distal section of the introducer lumen 74. The tubular distal electrode support 128 abuts the introducer distal end 76 and extends distally from the introducer distal end 76. The smaller diameter pusher catheter 94 is inserted from the proximal end of the introducer through the proximal portion of the introducer lumen 74 until the pusher catheter distal end 96 abuts the proximal stent end 242 of the compressed mesh retention stent 230. The lead body 212 is extended from its distal end within the distal lead support 228 proximally through the pusher catheter lumen 98.

During implantation, the assembly of the lead delivery mechanism 270 with the lead 200 illustrated in FIGS. 10 and 11 is advanced transvenously until the distal lead end 216 is located at the desired cardiac implantation site within the vessel lumen 64. The assembly may be rotated to a desired angular orientation of the distal and proximal electrodes 238 and 240 to the heart chamber if the electrodes 238 and 240 are shaped asymmetrically as in the embodiment of FIG. 1.

Then, the pusher catheter 94 is advanced distally within the introducer lumen 74 so that the pusher catheter distal end 96 pushes against the proximal stent end 242 and pushes the tubular mesh stent 230 distally and out of the introducer lumen 74 as shown in FIG. 12. The mesh stent 230 expands to its normal, expanded stent state from the compressed stent shape it was forced to assume when assembled within the introducer lumen 74. After it is completely expelled, the mesh stent 230 assumes the tubular expanded stent state configuration, and the lead delivery mechanism 270 is withdrawn over the lead body 212, as shown in FIG. 13.

The mesh stent 230 is shown having a mesh density that is higher in the central section of the stent than in proximal and distal stent sections adjacent to the proximal and distal stent ends 242 and 244 providing an expanded stent state stent wall that is more rigid in the central section than in the proximal and distal sections. The flexibility of the reduced density distal section that is attached to the proximal section of the tubular electrode support 228 by the stent retention wire 246 allows the more rigid central section to expand more readily and assume a tubular shape. The free proximal stent end 242 can expand further than the central section and engage firmly with the vessel wall.

In these embodiments of the invention, the retention stent 30, 130, 230 is not an electrode and is insulated from the electrode(s) formed on the exterior surface of or as part of the distal electrode support 28, 128, 228 as shown in FIG. 2. The distal electrode supports 28, 128, 228 are relatively inflexible and have a fixed support lumen diameter for the flow of blood therethrough and through the axially aligned stent lumens of the expanded retention stents. The expanded stent state diameters of the retention stents and the diameters of the distal electrode supports are selected to fit within but distend the vessel lumen somewhat so that the expanded retention stents advantageously firmly engage the vessel wall and the distal electrode(s) are in contact with the vessel wall rather than in the blood stream.

This arrangement also advantageously provides for a fixed distance between the proximal and distal electrodes when both are employed in order to provide a near field sensing axis that can be precisely positioned with respect to a selected heart chamber. The proximal and distal electrodes are spaced apart from one another by a close spacing that provides a bipolar, near field sensing axis or dipole for sensing the near field electrogram of the heart chamber that the electrodes are disposed toward in use. However, it will be understood that the leads 10, 100, 200 can be formed with a single distal electrode for use as a unipolar lead or only one of the electrodes can be employed for unipolar sensing and/or pacing.

Although the present invention is disclosed in the context of an endocardial lead locating at least one electrode in contact with a blood vessel wall, it will be understood that the invention can be practiced in any implantable lead adapted to locate and fix the electrode in contact with a tubular body organ wall including blood vessels, body tracts or ducts or the like.

While particular embodiments of the invention have been disclosed herein in detail, this has been done for the purposes of illustration only, and is not intended to limit the scope of the invention as defined in the claims which follow. It is to be understood that various substitutions, alterations, or modifications can be made to the disclosed embodiment without departing from the spirit and scope of the claims. The above described implementations are simply those presently preferred or contemplated by the inventors, and are not to be taken as limiting the present invention to the disclosed embodiments. It is therefore to be understood, that within the scope of the appended claims, the invention may be practiced otherwise than as specifically described without actually departing from the spirit and scope of the present invention.

We claim:

1. An implantable electrical lead for locating at least one distal electrode at a desired implantation site in a body vessel having a predetermined vessel diameter of the type comprising an elongated insulated lead body extending between a proximal lead end and a distal lead end and enclosing at least one electrical conductor having a proximal end and a distal end, the distal lead end further comprising:

a tubular electrode support coupled to said distal lead end having a fixed tubular support outer tall diameter and having a tubular support lumen extending between a proximal support end and a distal support end;

a first electrode coupled with said electrical conductor and supported on said tubular electrode support outer wall; and a tubular retention stent mounted to and extending axially from said tubular electrode support, said retention stent having a retention stent lumen axially aligned with said tubular support lumen, said retention stent adapted to assume a collapsed stent state having a collapsed stent diameter smaller than the vessel diameter to enable introduction of said distal lead end to said desired implantation site and to assume an expanded stent state having an expanded stent diameter sufficient to engage the retention stent against the body vessel to inhibit movement, whereby the aligned retention stent lumen and tubular support lumen enable flow of body fluids therethrough.

2. The electrical lead of claim 1, wherein said fixed tubular support outer wall diameter is correlated to the body vessel diameter such that the support outer wall engages the body vessel and said first electrode is placed in contact with the body vessel.

3. The electrical lead of claim 2, wherein:

said tubular electrode support is non-conductive; and said lead body encloses a second lead conductor extending from said proximal lead end to said distal lead end, and further comprising:

a second electrode supported by said tubular electrode support spaced from and electrically insulated from said first electrode and electrically connected to said second lead conductor at said distal lead end.

4. The electrical lead of claim 1, wherein:

said tubular electrode support is non-conductive; and said lead body encloses a second lead conductor extending from said proximal lead end to said distal lead end, and further comprising:

a second electrode supported by said tubular electrode support spaced from and electrically insulated from said first electrode and electrically connected to said second lead conductor at said distal lead end.

5. The electrical lead of claim 1, wherein said retention stent is formed of a tubular stent body adapted to be expanded from said collapsed stent state to said expanded stent state through the application of expansion force applied within said retention stent lumen while said retention stent is in said collapsed stent state.

6. The electrical lead of claim 1, wherein said retention stent is formed of a tubular stent body adapted to be restrained in said collapsed state and to expand from said collapsed stent state to said expanded stent state upon release of a restraint applied thereto.

7. An assembly to facilitate the advancement of an electrical lead within a patient's body to position and fix a first distal electrode of the electrical lead at a desired implantation site in an elongated body vessel, the electrical lead including a lead body extending between a proximal lead end and a distal lead end and a first lead conductor extending within said lead body between said proximal and distal lead ends and electrically connected to said first distal electrode, said arrangement comprising:

a tubular electrode support coupled to said distal lead end having a fixed tubular support outer wall supporting said first electrode, said tubular electrode support having an outer wall diameter and having a tubular support lumen extending between a proximal support end and a distal support end; and a tubular retention stent mounted to and extending axially from said tubular electrode support, said retention stent having a retention stent lumen axially aligned with said tubular support lumen and adapted to assume a collapsed stent state having a collapsed stent diameter smaller than the vessel diameter to enable introduction of said distal lead end to said desired implantation site and to assume an expanded stent state having an expanded stent diameter sufficient to engage the retention stent against the body vessel to inhibit movement; and lead delivery means for engaging and advancing said distal lead end to the desired implantation site with said retention stent in said collapsed stent state, said lead delivery means further comprising means for effecting the expansion of said retention stent from said collapsed stent state to said expanded stent state and for releasing said distal lead end at the desired implantation site, whereby the aligned retention stent lumen and tubular support lumen enable flow of body fluids therethrough.

8. The assembly of claim 7, wherein:

said retention stent is formed of a tubular stent body formed of a bent wire adapted to be expanded from said collapsed stent state to said expanded stent state through the application of expansion force applied within said retention stent lumen while said retention stent is in said collapsed stent state; and said lead delivery means further comprises expansion force applying means for selectively applying expansion force within said retention stent lumen while said retention stent is in said collapsed stent state and at said desired implantation site to expand said tubular stent body from said collapsed stent state to said expanded stent state.

9. The assembly of claim 8, herein said expansion force applying means further comprises:

a balloon catheter having an expandable balloon fitted within said retention stent lumen adapted to be expanded to apply expansion force to said retention stent while said retention stent is in said collapsed stent state and at said desired implantation site to expand said tubular stent body from said collapsed stent state to said expanded stent state.

10. The assembly of claim 8, herein said expansion force applying means further comprises:

a balloon catheter having an expandable balloon fitted within said retention stent lumen adapted to be expanded to apply expansion force to said retention stent while said retention stent is in said collapsed stent state and at said desired implantation site to expand said tubular stent body from said collapsed stent state to said expanded stent state; and an introducer having an introducer lumen for receiving said lead body and said balloon catheter coupled with said retention stent while said retention stent is in said collapsed stent state with said expandable balloon fitted within said retention stent lumen, whereby, upon advancement of the introducer to the desired implantation site, the retention stent and the balloon of the balloon catheter are adapted to be advanced distally from the introducer lumen and the balloon inflated to apply expansion force to said retention stent when said retention stent is in said collapsed stent state and at said desired implantation site to expand said tubular stent body from said collapsed stent state to said expanded stent state.

11. The assembly of claim 7, wherein:

said retention stent is formed of a tubular stent body adapted to be expanded from said collapsed stent state to said expanded stent state through the application of expansion force applied within said retention stent lumen while said retention stent is in said collapsed stent state; and said lead delivery means further comprises expansion force applying means for selectively applying expansion force within said retention stent lumen while said retention stent is in said collapsed stent state and at said desired implantation site to expand said tubular stent body from said collapsed stent state to said expanded stent state.

12. The assembly of claim 11, wherein said expansion force applying means further comprises:

a balloon catheter having an expandable balloon fitted within said retention stent lumen adapted to be expanded to apply expansion force to said retention stent while said retention stent is in said collapsed stent state and at said desired implantation site to expand said tubular stent body from said collapsed stent state to said expanded stent state.

13. The assembly of claim 11, wherein said expansion force applying means further comprises:

a balloon catheter having an expandable balloon fitted within said retention stent lumen adapted to be expanded to apply expansion force to said retention stent while said retention stent is in said collapsed stent state and at said desired implantation site to expand said tubular stent body from said collapsed stent state to said expanded stent state; and an introducer having an introducer lumen for receiving said lead body and said balloon catheter coupled with said retention stent while said retention stent is in said collapsed stent state with said expandable balloon fitted within said retention stent lumen, whereby, upon advancement of the introducer to the desired implantation site, the retention stent and the balloon of the balloon catheter are adapted to be advanced distally from the introducer lumen and the balloon inflated to apply expansion force to said retention stent when said retention stent is in said collapsed stent state and at said desired implantation site to expand said tubular stent body from said collapsed stent state to said expanded stent state.

14. The assembly of claim 13, wherein said retention stent extends proximally from the proximal support end of said tubular electrode support, said lead body extends proximally from said tubular electrode support and through said stent lumen, and said tubular electrode support extends distally from a distal end of said introducer when said retention stent and balloon catheter are received within said introducer lumen.

15. The assembly of claim 7, wherein said retention stent is formed of a tubular stent body adapted to be restrained in said collapsed state and to expand from said collapsed stent state to said expanded stent state upon release of a restraint applied thereto; and said lead delivery means further comprises restraining force applying means for selectively applying restraining force to said retention stent to maintain said retention stent is in said collapsed stent state and restraining force release means for releasing the restraining force at said desired implantation site to allow said tubular stent body to expand from said collapsed stent state to said expanded stent state.

16. The assembly of claim 15, wherein:

said restraining force applying means further comprises an introducer having an introducer lumen for receiving said lead body extending therethrough and said retention stent in a distal portion of said introducer lumen while said retention stent is in said collapsed stent state; and said release means further comprises a pusher catheter adapted to be advanced distally through said introducer lumen and to push against and move said retention stent distally out of said distal portion of said introducer lumen while said retention stent is in said collapsed stent state, thereby releasing the restraining force applied to said retention stent to allow said tubular stent body to expand from said collapsed stent state to said expanded stent state.

17. The assembly of claim 16, wherein said retention stent extends proximally from the proximal support end of said tubular electrode support, said lead body extends proximally from said tubular electrode support and through said stent lumen, and said tubular electrode support extends distally from a distal end of said introducer when said retention stent is received within said distal portion of said introducer lumen.

18. A method of advancing and fixing a first distal electrode of an electrical lead within a patient's body at a desired implantation site in an elongated body vessel, the electrical lead including a lead body extending between a proximal lead end and a distal lead end and a first lead conductor extending within said lead body between said proximal and distal lead ends and electrically connected to said first distal electrode, said arrangement comprising:

providing a tubular electrode support coupled to said distal lead end having a fixed tubular support outer wall supporting said first electrode, said tubular electrode support having an outer wall diameter and having a tubular support lumen extending between a proximal support end and a distal support end;

providing a tubular retention stent mounted to and extending axially from said tubular electrode support, said retention stent having a retention stent lumen axially aligned with said tubular support lumen and adapted to assume a collapsed stent state having a collapsed stent diameter smaller than the vessel diameter to enable introduction of said distal lead end to said desired implantation site and to assume an expanded stent state having an expanded stent diameter sufficient to engage the retention stent against the body vessel to inhibit movement;

engaging and advancing said distal lead end to the desired implantation site with said retention stent in said collapsed stent state;

effecting the expansion of said retention stent from said collapsed stent state to said expanded stent state, whereby the aligned retention stent lumen and tubular support lumen enable flow of body fluids therethrough.

19. The method of claim 18, further comprising the step of:

forming said retention stent of a tubular stent body adapted to be expanded from said collapsed stent state to said expanded stent state through the application of expansion force applied within said retention stent lumen while said retention stent is in said collapsed stent state; and said effecting step further comprises:

selectively applying expansion force within said retention stent lumen said retention stent is in said collapsed stent state and at said desired implantation site to expand said tubular stent body from said collapsed stent state to said expanded stent state.

20. The method of claim 19, wherein said engaging and advancing step further comprises the step of:

inserting a balloon catheter having an expandable balloon within said retention stent lumen while said retention stent is in said collapsed stent state; and advancing said balloon catheter and said distal lead end to the desired implantation site; and said expansion force applying step further comprises the steps of:

expanding the expandable balloon at said desired implantation site to apply expansion force to said retention stent to expand said tubular stent body from said collapsed stent state to said expanded stent state.

21. The method of claim 19, wherein said engaging and advancing step further comprises the step of:

inserting a balloon catheter having an expandable balloon within said retention stent lumen while said retention stent is in said collapsed stent state;

inserting the balloon catheter and said lead into an introducer lumen with said expandable balloon and said retention stent while said retention stent is in said collapsed stent state;

advancing said introducer, said balloon catheter, and said distal lead end to the desired implantation site; and ejecting said expandable balloon and said retention stent distally from said introducer lumen; and said expansion force applying further comprises the steps of:

expanding the expandable balloon at said desired implantation site to apply expansion force to said retention stent to expand said tubular stent body from said collapsed stent state to said expanded stent state.

22. The method of claim 18, further comprising the step of:

forming said retention stent of a tubular stent body adapted to be restrained in said collapsed state and to expand from said collapsed stent state to said expanded stent state upon release of a restraint applied thereto; and said effecting step further comprises:

selectively applying restraining force to said retention stent to maintain said retention stent is in said collapsed stent state; and releasing the restraining force at said desired implantation site to allow said tubular stent body to expand from said collapsed stent state to said expanded stent state.

23. The method of claim 22, wherein:

said restraining force applying step further comprises locating said lead body extending through an introducer lumen of an elongated introducer with said retention stent restrained in said collapsed stent state in a distal portion of said introducer lumen; and said releasing step further comprises advancing a pusher catheter distally through said introducer lumen to push against and move said retention stent distally out of said distal portion of said introducer lumen while said retention stent is in said collapsed stent state, thereby releasing the restraining force applied to said retention stent to allow said tubular stent body to expand from said collapsed stent state to said expanded stent state.

24. The method of claim 18, wherein said body vessel constitutes the coronary sinus of the heart and body fluids constitute venous blood.

25. The method of claim 18, wherein said body vessel constitutes the great vein descending from the coronary sinus of the heart and body fluids constitute venous blood.

* * * * *

UNITED STATES PATENT AND TRADEMARK OFFICE
CERTIFICATE OF CORRECTION

PATENT NO. : 6,161,029
DATED : December 12, 2000
INVENTOR(S) : Spreigl et al.

It is certified that error appears in the above-identified patent and that said Letters Patent is hereby corrected as shown below:

<u>Title page,</u>
Item [75] Inventors: "Chester I. Struble" should read -- Chester L. Struble
Item [75] Inventors: "Paulus C. von Venrooij" should read -- Paulus C. Van Venrooij --

Signed and Sealed this

Thirtieth Day of October, 2001

Attest:

NICHOLAS P. GODICI
Attesting Officer
Acting Director of the United States Patent and Trademark Office